(12) United States Patent
Dupont et al.

(10) Patent No.: US 7,682,569 B2
(45) Date of Patent: Mar. 23, 2010

(54) SYSTEM EQUIPPED WITH WATER PURIFICATION MEANS

(75) Inventors: Stéphane Dupont, Elancourt (FR); Yves Gaignet, Montigny le Bretonneux (FR)

(73) Assignee: Millipore Corporation, Billerica, MA (US)

( * ) Notice: Subject to any disclaimer, the term of this patent is extended or adjusted under 35 U.S.C. 154(b) by 1037 days.

(21) Appl. No.: 10/853,841

(22) Filed: May 26, 2004

(65) Prior Publication Data

US 2005/0013739 A1      Jan. 20, 2005

(30) Foreign Application Priority Data

Jul. 18, 2003    (FR)    .................... 03 08812

(51) Int. Cl.
*B01L 99/00*    (2010.01)
(52) U.S. Cl. ...................................... 422/101
(58) Field of Classification Search .................. 422/101
See application file for complete search history.

(56) References Cited

U.S. PATENT DOCUMENTS 5,571,419 A * 11/1996 Obata et al. ................. 210/664

5,585,003 A * 12/1996 Van Newenhizen ......... 210/646
6,197,255 B1   3/2001 Miyake
6,649,037 B2 * 11/2003 Liang et al. ................. 204/632

FOREIGN PATENT DOCUMENTS

JP      06265555 3      9/1994
JP      2000266763      9/2000

OTHER PUBLICATIONS

English Translation of JP2000-266763. Dec. 2007.*

* cited by examiner

*Primary Examiner*—Walter D Griffin
*Assistant Examiner*—Bobby Ramdhanie

(57) ABSTRACT

The invention relates to an analyzer device of the kind using purified water and including one or more analyzer means adapted to carry out predetermined analyses and defining at least one point of use of the purified water and having a water purification system at least partially formed on board the device. The water purification system includes a variety of water purification modules adapted to produce purified water for the one or more analyzer means having a predetermined purity and in that the purified water is taken up by the one or more analyzer means immediately after it has been purified.

5 Claims, 2 Drawing Sheets

SYSTEM EQUIPPED WITH WATER PURIFICATION MEANS

Figure 1:
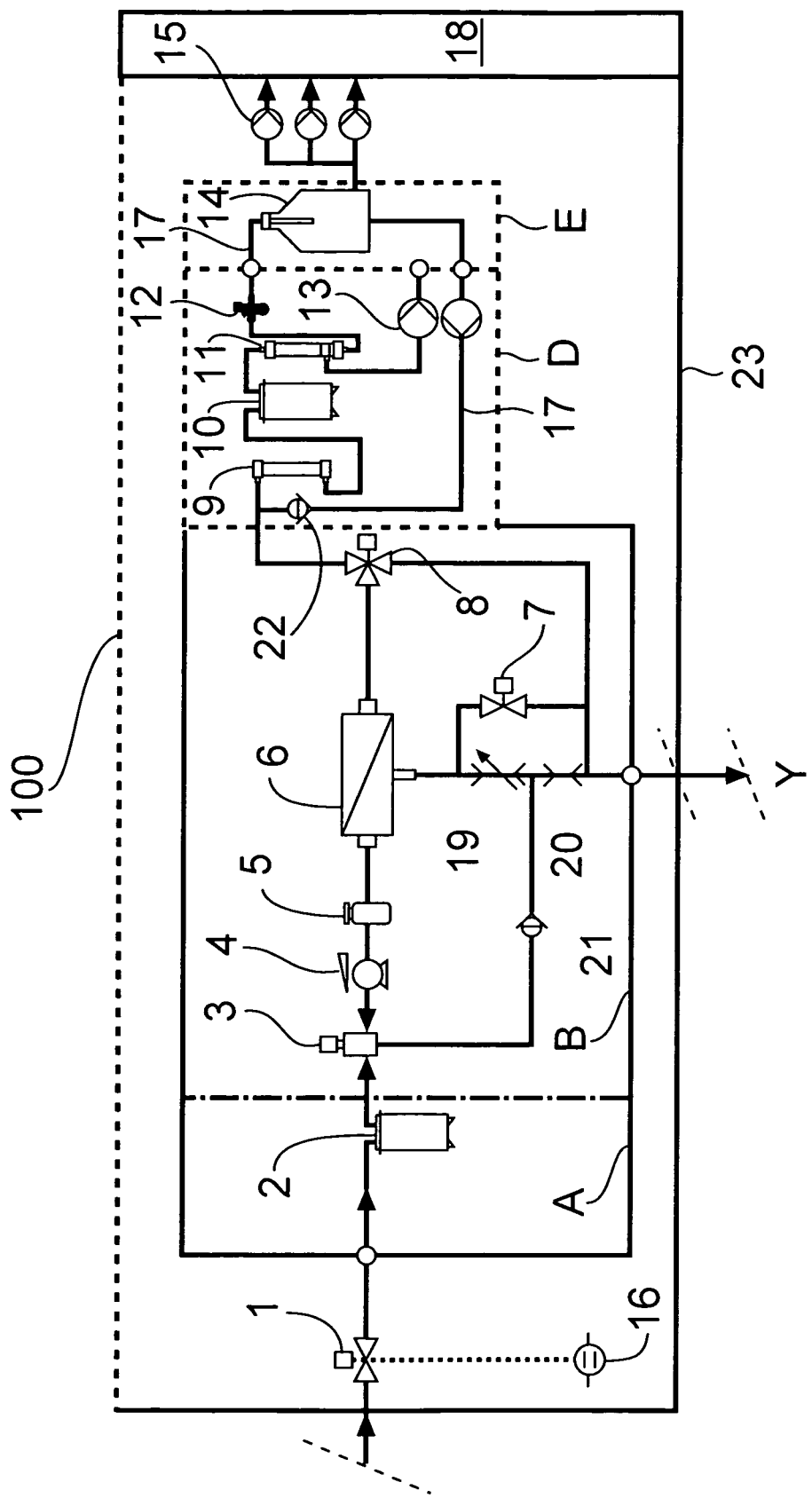

The present invention relates to an analyzer device of the kind using purified water, in particular for medical analyses.

BACKGROUND OF THE INVENTION

An analyzer device of the above kind is used to analyze blood, for example, to indicate if a given substance is present in the blood, and if so the corresponding concentration.

Conventional analyzer devices require pure water in particular:
   for cleaning bowls,
   for rinsing test tubes,
   for controlled temperature incubation baths,
   for built-in reagent regeneration devices, and
   for automatic dilution of samples.

The accuracy of an analysis can be decisive in the adoption of a treatment or the dosage of medication.

The water supply system must therefore supply points of use with water of a quality such that it does not influence the analysis results.

The US National Committee for Clinical Laboratory Standards (NCCLS) issues a document entitled "*Preparation and testing of reagent water in the clinical laboratory*" defining the quality of the water that must be used in the field of medical analyses, the influence of contaminants on the results of analyses, the preferred method of maintaining a particular quality of the water, the manner of testing the water and the measures to be effected if it is suspected that the water has influenced the results of an analysis. In the above document, the NCCLS also defines three types of water:
   Type III: for rinsing glassware and basic applications;
   Type II: for ordinary use in analyzers; and
   Type I: for critical tests or tests where the influence of contaminated water on the results has not been determined with certainty.

As the influence of contaminants on the results of analyses is not well known, the NCCLS recommends using Type I water in analysis devices to prevent and eliminate all potential problems.

Existing autonomous water treatment systems connected to analyzer devices to supply them with water of given purity generally guarantee the quality of the water at the inlet of the analyzer devices. When water of Type I is stored, whether outside or inside the analyzer device, its resistivity decreases, metallic and/or organic contaminants pass from the storage tank to the water stored therein, and microbiological contamination occurs. The storage tank is generally inside the analyzer device in a warm environment (temperature from 30° C. to 37° C.), which further encourages the growth of bacteria.

Accordingly, the water reaching the points of use in the analyzer device no longer corresponds to the Type I requirements previously cited, even if, as suggested by the NCCLS, the water storage tank is agitated, the water storage tank in all prior art analyzer devices being a container into which purified water from the water treatment system is fed, and from which it is subsequently extracted by the analyzer device. This has the following consequences:
   poor results of analyses, and the consequences thereof for patients,
   the necessity to employ frequent cleaning procedures, and
   high maintenance and service costs.

Another problem in existing applications is that the water treatment system and the analyzer device do not exchange information, and prior art analyzer devices are not designed to monitor the quality of the water or to maintain it at a given quality.

The present invention aims to alleviate these problems.

SUMMARY OF THE INVENTION

To this end, the present invention consists in an analyzer device of the kind using purified water and including analyzer means adapted to carry out predetermined analyses and defining at least one point of use of the purified water, characterized in that it further includes water purification means adapted to produce purified water for said analyzer means having a predetermined purity and in that the purified water is taken up by the analysis means immediately after it has been purified.

Thanks to the above features, it is possible to monitor the quality of the water and to maintain a predetermined purity as far as the point of use at which analyses, chemical reactions, washing, etc. are carried out.

Furthermore, the present invention simplifies analyzer device decontamination procedures and guarantees improved reproducibility of tests and analyses.

In this regard, it is important to note that, in the context of the present invention, the water itself is considered as a reagent.

According to preferred features of the invention, some of which may be combined:
   the purified water is taken up by the analyzer means (i) directly at the outlet of the purification means, or (ii) from a recirculation loop for recirculating purified water from the purification means in at least one portion of the latter, or (iii) in a storage tank in the aforementioned recirculation loop (see (ii) above) and in which purified water from the purification means flows,
   the analyzer device operates in a closed circuit and the purification means are therefore adapted to recover spent water from one or more points of use,
   the device includes an inlet for water to be purified from a drinking water main, said purification means being connected to said inlet for water to be purified,
   the purification means are chosen in the group comprising pretreatment means, in particular using an active carbon filter, reverse osmosis purification means, electro-deionization means, UV radiation oxidation treatment means, polishing means, degassing means, final filtration means, and combinations thereof,
   the purification means include a final treatment subassembly of the water to be purified before leaving the purification means consisting in succession of said UV radiation oxidation treatment means, said polishing means, said degassing means, and said final filtration means, and the recirculation loop is connected to the inlet of the UV radiation oxidation treatment means,
   the analyzer means and the purification means include respective functionally interconnected electronic control units each adapted to control and monitor the means associated with it,
   the electronic control units of the analyzer means and the purification means are functionally interconnected to enable feedback from the control unit of the analyzer means to the control unit of the water purification means,
   the analyzer means and the purification means include a common control unit adapted to control and monitor the analyzer means and the purification means simultaneously,
   the water purification means form a unitary subassembly mounted in or connected to the analyzer device, and the analyzer means are adapted to carry out medical analyses.

Other features and advantages of the invention will emerge further from the following description, which is given by way of example and with reference to the accompanying diagrammatic drawings.

IN THE DRAWINGS

Figure 2:
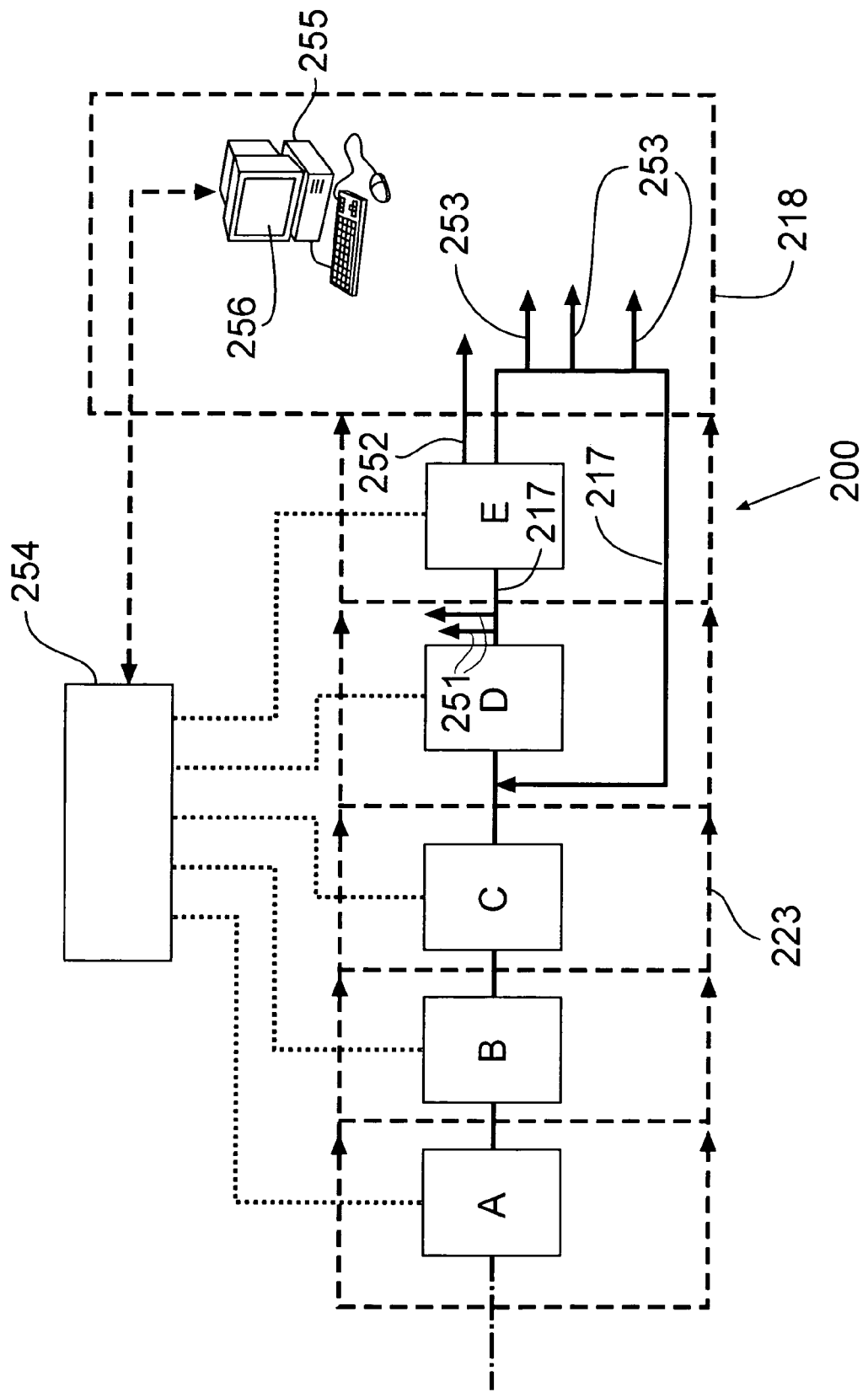

FIG. 1 is a diagram showing the structure of an analyzer device according to the invention, and FIG. 2 is a functional block diagram of an analyzer system according to the invention.

DETAILED DESCRIPTION OF THE INVENTION

In the embodiment shown in FIG. 1, the water to be purified preferably comes from a drinking water main and is fed into an analyzer device 100, referred to hereinafter for convenience as the analyzer, via an inlet solenoid valve 1 connected to a detector cell 16 for cutting off the power supply to the solenoid valve 1 in the event of a leakage of water in the analyzer 100. According to the invention, the analyzer 100 includes a system 23 for purifying water from the water main, which system includes firstly a pretreatment module 2 that is known in the art and that removes particles and free chlorine present in the water and can, where applicable, prevent the formation of limescale deposits on a reverse osmosis membrane described in more detail below.

This kind of pretreatment module contains, for example, grains of activated carbon, front-end prefiltration elements and the like as are known to one of skill in the art.

The water pretreated in this way is fed to a reverse osmosis module 6. This module is also known in the art and is not in itself particularly relevant to the present invention. However, note that in practice the flow of water to be purified is continuous and tangential to a membrane of the reverse osmosis module 6, with the result that the water to be purified is divided at the membrane into two portions with different concentrations:

a portion that passes through the membrane, also known as the permeate, and a portion that does not pass through the membrane, also known as the retentate, and which contains ions, molecules or particles retained by the membrane, in particular mineral ions.

The osmosis module is preceded by a pressure regulator 3 for regulating the pressure at the inlet of the reverse osmosis module, generally to 2 bar. The water is then fed by a pump 4 to the reverse osmosis module 6 at a predetermined pressure and flowrate to guarantee a constant flow of permeate at a temperature from 5° C. to 30° C.

A device 5 for introducing an agent for cleaning the reverse osmosis membrane and the pipes is provided between the pump 4 and the reverse osmosis module 6.

A portion of the retentate passes through a flowrate regulator 19 and is returned to the pressure regulator 3 via a check valve 21 and another portion of said retentate is drained off via a flowrate limiter 20.

Furthermore, a rinsing valve 7 on the upstream side of the reverse osmosis membrane maintains good purification performance.

In normal operation, the flowrate regulator 19 and the pressure regulator 3 maintain a constant pressure on the upstream side of the reverse osmosis membrane. The flowrate limiter 20 in series with the flowrate regulator 19 limits the flowrate to a maximum value specific to it, even when the regulator 19 is fully open. There is therefore always a counterpressure that ensures the pressure necessary for correct operation of the reverse osmosis module 6.

When the valve 7 is opened, there is no longer any significant restriction of flow, and the water entering the reverse osmosis module 6 is no longer subject to any counterpressure from the regulator 19. Accordingly, most of the water leaves the module 6 before it has passed through the membrane and expels the impurities deposited thereon to the drain via the valve 7.

On closing said valve 7, the regulator 3 and the pump 4 reestablish a counterpressure on the upstream side of the membrane of the reverse osmosis module 6, which then operates normally again.

A three-way solenoid valve 8 at the outlet of the reverse osmosis module 6:

drains away any water that does not satisfy the predetermined quality criteria, and sends purified water to subsequent purification phases.

In the latter case, the water passes successively through a UV radiation oxidation treatment module 9 (wavelength 185 nm), a polishing module 10, a degassing module 11 and, finally, a final filtration element 12 with a mesh size of 0.22 μm. Each of these filtration techniques being known in the art, they are not described in further detail here.

The purified water at the outlet of the filter 12 is directed into a storage tank 14 equipped with a sterilization UV lamp (wavelength 254 nm) to maintain a low level of bacteria therein.

In accordance with the invention, the storage tank 14 is in fluid communication with the inlet of the UV treatment module 9 to cause the water in the final purification section to flow in a loop (the recirculation loop 17 integrates the storage tank 14), thanks in particular to a recirculation pump 13 and a check valve 22. This means that the purified water in the storage tank is constantly renewed and of maximum purity. The pump 13 also provides the vacuum pump function necessary for operation of the degassing module 11.

The points of use of the analyzer system 18 of the analyzer 100 are supplied via a distributor 15 connected to the storage tank 14, which ensures that whenever the device is operating (under steady state conditions) the water distributed to the points of use is of high quality, in practice of Type I purity.

This analysis section 18 includes analysis means generally used in prior art analyzers and for this reason are not described in more detail here. Likewise the electronic control means of the purification system 23 and the analyzer system 18 of the analyzer 100 are not described in more detail here. However, one embodiment of the latter is described next with reference to FIG. 2.

As shown by the dashed line arrows in FIG. 2, the water purification system 223 can be entirely or partly within the analyzer 200.

Furthermore, depending on the chosen embodiment of the invention, the water purification system 223 can have various configurations:

a system entirely integrated into the analyzer, a system forming a subassembly mounted in the analyzer, or a system connected to the analyzer.

Turning to FIG. 2, purification is carried out in four units A to D, and a storage tank E is integrated into the recirculation loop 217 leading to the unit D.

As in FIG. 1, purification of the water starts in a pretreatment module A. This is followed by treatment in a reverse osmosis module (unit B) and treatment in an electro-deionization module (unit C). The latter being also well known in the art, it is not described in more detail here. Finally, final purification in the unit D utilizes the following means:

UV radiation oxidation,
ion exchange resin polishing,
degassing, and
final filtration.

It is therefore at the outlet of the unit D that the water has the highest quality that can be obtained in the water treatment system. In practice it is water of Type I.

Note that the above units are also shown in FIG. 1, except for the unit C, as this is optional.

Note also that there are several possible positions for connecting the points of use. They can be connected directly to the outlet of the unit D (arrows 251) or by a dead arm directly to the outlet of the buffer storage tank E (arrow 252), providing a temporary high flowrate, for example. The latter configuration corresponds to that of FIG. 1.

The point(s) of use can also be connected directly to take-off points on the recirculation loop 217 (arrows 253), with no "dead arm".

It is important to note that in all cases the path between the point(s) of use and the outlet of the unit D is optimized to guarantee the predetermined water quality at the point(s) of use.

The continuous water recirculation loop 217 leading to the module D, into which the storage tank E is integrated in the FIG. 2 embodiment, also ensures a continuously high quality of the water supplied to the point(s) of use.

In the embodiment shown in FIG. 2, there is an electronic control unit 254 for the modules A-D of the water treatment system, which is functionally connected to a central unit 255 of the analyzer system 218 of the analyzer 200.

The user can therefore have continuously available on a screen 256 connected to the central unit 255 information on the water quality at the outlet of the unit D and/or the various points of use, together with alarm, breakdown and scheduled maintenance signals.

Moreover, the central unit 255 of the analyzer 200 can operate on the water treatment system 223 via the control unit 254 and modify various parameters thereof to adapt the water at the outlet of the unit D to its requirements in real time.

Note also that, for simplicity, sensors for measuring the conductivity and the temperature of the water functionally connected to the control portion of the unit 254, which determine the purity of the water at predetermined locations, such as the outlet of the unit D, are not shown in FIGS. 1 and 2.

Other optional sensors can also be used (to measure the concentration of dissolved oxygen, of total biological carbon, etc.).

It must be understood that the present invention is in no way limited to the embodiments described hereinabove and that many modifications can be made thereto without departing from the scope of the invention.

In particular, in a different embodiment, water can be sent farther upstream in the purification process (to the inlet of the unit A, B or C), or supplementary purification means can be used, for example ultrafiltration means.

The invention claimed is:

1. An analyzer device using purified water and including one or more analyzer means for carrying out predetermined analyses and defining at least one point of use of the purified water in the analyzer means comprising an analyzer device having one or more analyzer means and a water purification system adapted to produce purified water for said one or more analyzer means having a predetermined purity and in that the purified water is taken up by the one or more analyzer means immediately after it has been purified wherein the purified water is taken up by the one or more analyzer means directly at the outlet of the purification system and further comprising a final filtration module located adjacent the outlet of the purification system.

2. The analyzer device according to claim 1 wherein the purification system is formed of a pretreatment module, a reverse osmosis purification module, an electro-deionization module and a final filtration module wherein the final filtration module consists essentially of an UV radiation oxidation treatment module, polishing module, degassing module.

3. An analyzer device using purified water and including one or more analyzer means for carrying out predetermined analyses and defining at least one point of use of the purified water in the analyzer means comprising an analyzer device having one or more analyzer means and a water purification system adapted to produce purified water for said one or more analyzer means having a predetermined purity, the analyzer taking the purified water from an outlet from the purification system and wherein the purification system includes a final treatment subassembly for the water to be purified before leaving the purification system consisting in succession of an UV radiation oxidation treatment device, a polishing device, a degassing device and a final filtration device, the final treatment subassembly outlet being connected to a storage tank and wherein a recirculation loop is connected to the inlet of the UV radiation oxidation treatment means from the storage tank and the outlet to the analyze from the purification system is located on the storage tank.

4. An analyzer device using purified water and including one or more analyzer means for carrying out predetermined analyses and defining at least one point of use of the purified water in the analyzer means comprising an analyzer device having one or more analyzer means and a water purification system adapted to produce purified water for said one or more analyzer means having a predetermined purity and in that the purified water is taken up by the one or more analyzer means immediately after it has been purified wherein the purified water is taken up by the one or more analyzer means directly at the outlet of the purification system, the purification system having a recirculation loop for recirculating purified water of the purification system, a storage tank in the recirculation loop, wherein the purification system is formed of a pretreatment module, a reverse osmosis purification module, an electro-deionization module and a final filtration module, wherein the final filtration module consists essentially of an UV radiation oxidation treatment module, polishing module, degassing module and final filtration and wherein the final filtration module is connected to the outlet of the purification system and to the recirculation loop before the storage tank and the storage tank is attached to the purification system before the final filtration module.

5. An analyzer device using purified water and including one or more analyzer means for carrying out predetermined analyses and defining at least one point of use of the purified water in the analyzer means comprising an analyzer device having one or more analyzer means and a water purification system adapted to produce purified water for said one or more analyzer means having a predetermined purity and in that the purified water is taken up by the one or more analyzer means immediately after it has been purified wherein the purified water is taken up by the one or more analyzer means directly at the outlet of the purification system wherein the purification system includes a final treatment subassembly for the water to be purified before leaving the purification system consists essentially of in succession of an UV radiation oxidation treatment device, a polishing device, a degassing device and a final filtration device, the final treatment subassembly outlet being connected to a storage tank and wherein a recirculation loop is connected to the inlet of the UV radiation oxidation treatment means from the storage tank.

* * * * *